United States Patent [19]

Naylor

[11] 4,158,863
[45] Jun. 19, 1979

[54] INPUT OVERLOAD PROTECTION CIRCUIT

[75] Inventor: Thomas K. Naylor, Belmont, Mass.

[73] Assignee: American Optical Corporation, Southbridge, Mass.

[21] Appl. No.: 884,326

[22] Filed: Mar. 7, 1978

[51] Int. Cl.$^2$ .............................................. H02H 7/20
[52] U.S. Cl. .................................. 361/56; 330/207 P; 361/91
[58] Field of Search ...................... 361/56, 90, 91, 111; 330/207 P

[56] References Cited

U.S. PATENT DOCUMENTS

| 3,979,642 | 9/1976 | Cath et al. ............................ 361/56 |
| 4,044,313 | 8/1977 | Wittlinger et al. ................ 330/207 P |
| 4,068,278 | 1/1978 | Williams ................................ 361/56 |

FOREIGN PATENT DOCUMENTS

| 2341378 | 4/1974 | Fed. Rep. of Germany ....... 330/207 P |
| 2110677 | 7/1977 | Fed. Rep. of Germany ............. 361/56 |

Primary Examiner—Harry E. Moose, Jr.
Attorney, Agent, or Firm—Jeremiah J. Duggan; Stephen A. Schneeberger

[57] ABSTRACT

An input overload protection circuit particularly suited for use with a high impedance differential amplifier having two inputs is provided. The protection circuit prevents the flow of substantially all leakage currents for input signals within the linear operating range of the amplifier, and includes a first and second serial plurality of diode-action clamping means, such as diodes, connected respectively between the first and second input conductors to the amplifier input and a third conductor connected to a reference potential. Driven guard means operate to apply the voltage appearing on the respective first and second input conductors at their junction with the respective first and second clamping means to the respective first and second plurality of clamping means intermediate the respective ends thereof, thereby to substantially prevent leakage current from flowing through the clamping means from the pair of conductors.

6 Claims, 2 Drawing Figures

INPUT OVERLOAD PROTECTION CIRCUIT

BACKGROUND OF THE INVENTION

The invention relates generally to overload protection circuitry and more specifically to input overload protection circuitry for a high impedance differential amplifier.

Amplifiers generally, and differential amplifiers more specifically, find extensive application in a wide variety of circuits and systems. High impedance differential amplifiers particularly find application in a large variety of instruments and are commonly referred to as instrumentation amplifiers. Such amplifiers typically receive a small amplitude signal from a transducer or the like and provide the first stage or stages of amplification. In one significant field of application, such instrumentation amplifiers are used to receive and amplify physiological waveforms, such as the electrocardiographic waveforms of a patient. Still further, there may be instances when the input signal exceeds the linear range of the amplifier, as for instance during defibrillation of a patent and/or establishment of electrolyte equilibrium in a patient following the placement of sensing electrodes, and the like. In such instances, it is often desirable and even necessary to prevent such excessive voltages from appearing at the amplifier inputs in order to preserve the integrity of the amplifier. Further, other elements such as CMOS switches and the like in the amplifier's input circuitry may be damaged by the excessive voltages. Accordingly, clamping diodes have been connected across the amplifier input to effectively short circuit excessive signal voltages, thereby protecting the amplifier. Typically, such diode clamping circuits have been entirely passive and have served effectively to short circuit large voltages appearing at the amplifier input. However, that very diode clamping circuit may serve to distort the input signal passed to the amplifier because of some current leakage through the diodes. That leakage, though small, may have a significant effect upon the information signal, particularly where there is a large series resistance in the current path between the patient and the clamping diodes.

Several techniques have evolved for minimizing or preventing leakage currents in clamping networks and tend to vary somewhat with the type of amplifier that's being protected. In addition to purely passive clamping networks, some have applied reverse bias to the diodes which, however, still permits some leakage and resulting distortion to the input signal. Other methods use feedback diodes which require high current drivers to absorb transients. One recent technique which effectively and relatively inexpensively suppresses leakage currents during linear operation is that embodied in the input circuitry of the PULSAR ® 4000 Defibrillator of American Optical Corporation, 36 Crosby Drive, Bedford, Mass. In that instrument, a substantially zero voltage drop across one or more of the diode elements is actively maintained to prevent the flow of leakage currents during normal operation. However, that particular circuit was applicable only to single-ended amplifiers where rejection of common mode voltage is not a problem. Accordingly, it is a principal object of the present invention to provide an input overload protection circuit for a differential amplifier. It is a further object to provide an input overload protection circuit which substantially eliminates the flow of leakage currents during normal linear operation of a high impedance differential amplifier requiring protection.

These and other objects of the invention will be in part obvious and in part pointed out in greater detail hereinafter.

SUMMARY OF THE INVENTION

In accordance with the present invention, there is provided an input overload protection circuit particularly suited for use with a high impedance differential amplifier having a pair of inputs. The protection circuit prevents the flow of substantially all leakage currents for input signal voltages within the linear operating range of the amplifier. The protection circuit includes a first and second serial plurality of diode-action clamping means, such as diodes, connected respectively between the first and second input conductors to the amplifier input and a third conductor connected to a reference potential. Driven guard means operate to apply the voltage appearing on the respective first and second input conductors at their junction with the respective first and second clamping means to the respective first and second plurality of clamping means intermediate the respective ends thereof, thereby to substantially prevent leakage current from flowing through the clamping means from the pair of conductors.

In a preferred embodiment, at least one of the diode-action clamping means in both the first and second serial pluralities of clamping means is common to both said serial pluralities, that common clamping means being at least that one connected most directly to the third or reference conductor.

The differential amplifier includes a pair of operational amplifiers each having a different one of the pair of input conductors respectively connected to the noninverting input thereof and applying substantially the same signal voltage appearing at the junction of the conductor with the respective clamping means. A first voltage divider network is connected with its opposite ends to the respective outputs of the pair of operational amplifiers and includes first and second spaced taps thereon respectively connected to the inverting inputs of the operational amplifiers for completing respective feedback paths thereto. The voltages then appearing at the first and second taps on the voltage divider are substantially the same as the signal voltages appearing on the respective input conductors to the respective operational amplifiers. A second voltage divider network also having a pair of spaced taps and scaled proportionally identical to the first divider is connected in parallel with that divider. The first and second taps of the second divider are connected to the respective first and second serial plurality of clamping diodes intermediate the respective opposite ends thereof to prevent leakage currents from the input conductors through the clamping diodes.

DESCRIPTION OF A PREFERRED EMBODIMENT

Figure 1:
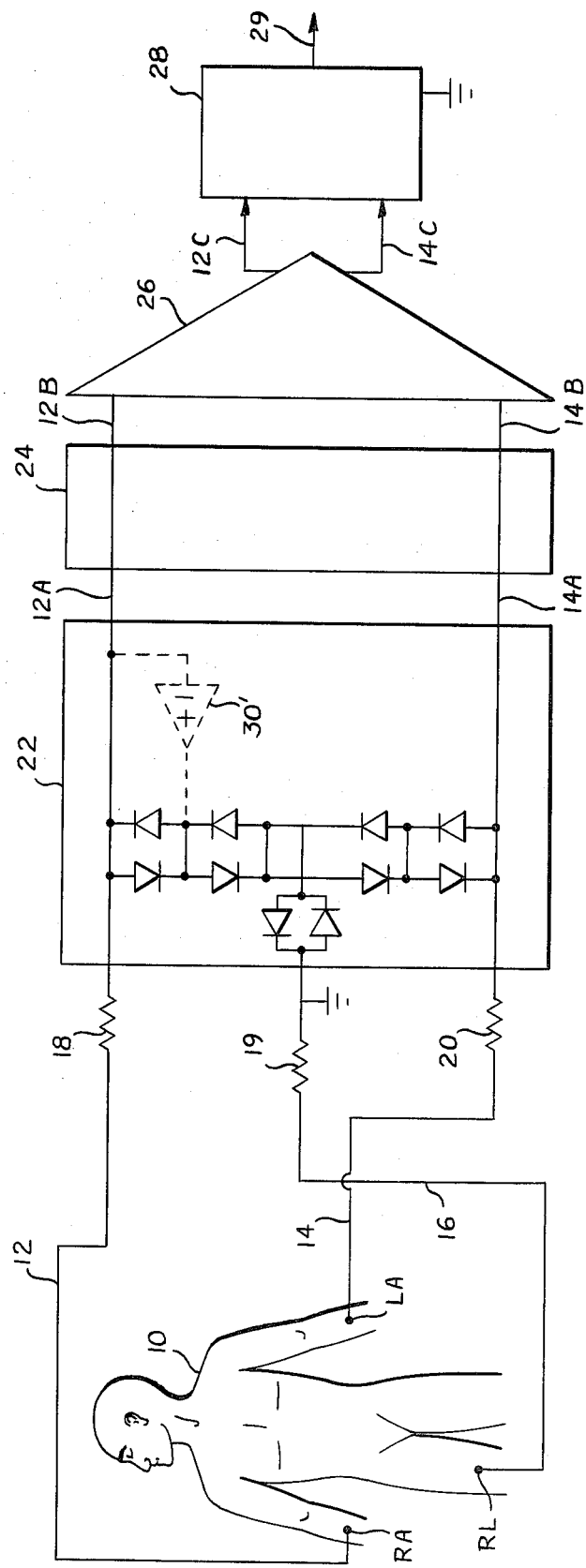
FIG. 1 is a symbolic schematical block diagram illustrating an amplifier and the overload protection circuit of the invention.

Referring to FIG. 1, electrical potentials representative of the electrocardiogram of patient 10 are sensed by electrodes RA, LA and RL and extended via conductors 12, 14 and 16 respectively to the input circuitry and amplifiers of processing instrumentation. Typically, that instrumentation will require an accurate amplified replica of the potential difference between the electropotentials at the right arm (RA) and the left arm (LA). Generally speaking, the potentials sensed by electrodes RA and LA are conducted by conductors 12 and 14 respectively through respective series input resistors 18 and 20, past protection circuitry 22 and calibration switches 24 to respective inputs of a differential amplifier or preamplifier 26. The double-ended output of amplifier 26 provides the inputs to a further differential amplifier 28 having a single-ended output 29 referenced to ground. Because of certain series circuit elements appearing in conductors 12 and 14, those input conductors receive the designations 12A and 14A respectively following input resistors 18 and 20 respectively, they receive the designations 12B and 14B respectively following the calibration switching circuitry 24, and they bear the designations 12C and 14C respectively upon output from differential amplifier 26. Following the voltage drops across input resistors 18, 20 the signal potentials at 12A, 14A respectively remain substantially constant to the outputs 12C, 14C.

The input protection circuitry 22 of FIG. 1 illustrates the diode clamping network thereof as it actually appears in a preferred embodiment; however, the driven guard circuitry associated therewith is illustrated in symbolic fashion and identified by the reference numeral 30'. Furthermore, that guard circuitry 30' is, in FIG. 1, illustrated as being applied only to the clamping circuitry associated with one of the two input conductors to differential amplifier 26 whereas in fact it is applied to both. However, phantom guard circuit 30' does serve to illustrate the inventive technique of applying the potential appearing on conductor 12A to a segment of the diode clamping network such that there is no voltage drop across that segment of the network and thus no leakage current flow through it. The symbolic illustration shown in phantom in FIG. 1, although implemented somewhat differently in the preferred embodiment illustrated in FIG. 2, does indeed suggest one means of implementing the invention, that being simply with a unity gain amplifier as shown. That simplistic arrangement, while theoretically possible, has certain practical limitations because of the size and power requirements associated with the needed amplifier 30'.

Figure 2:
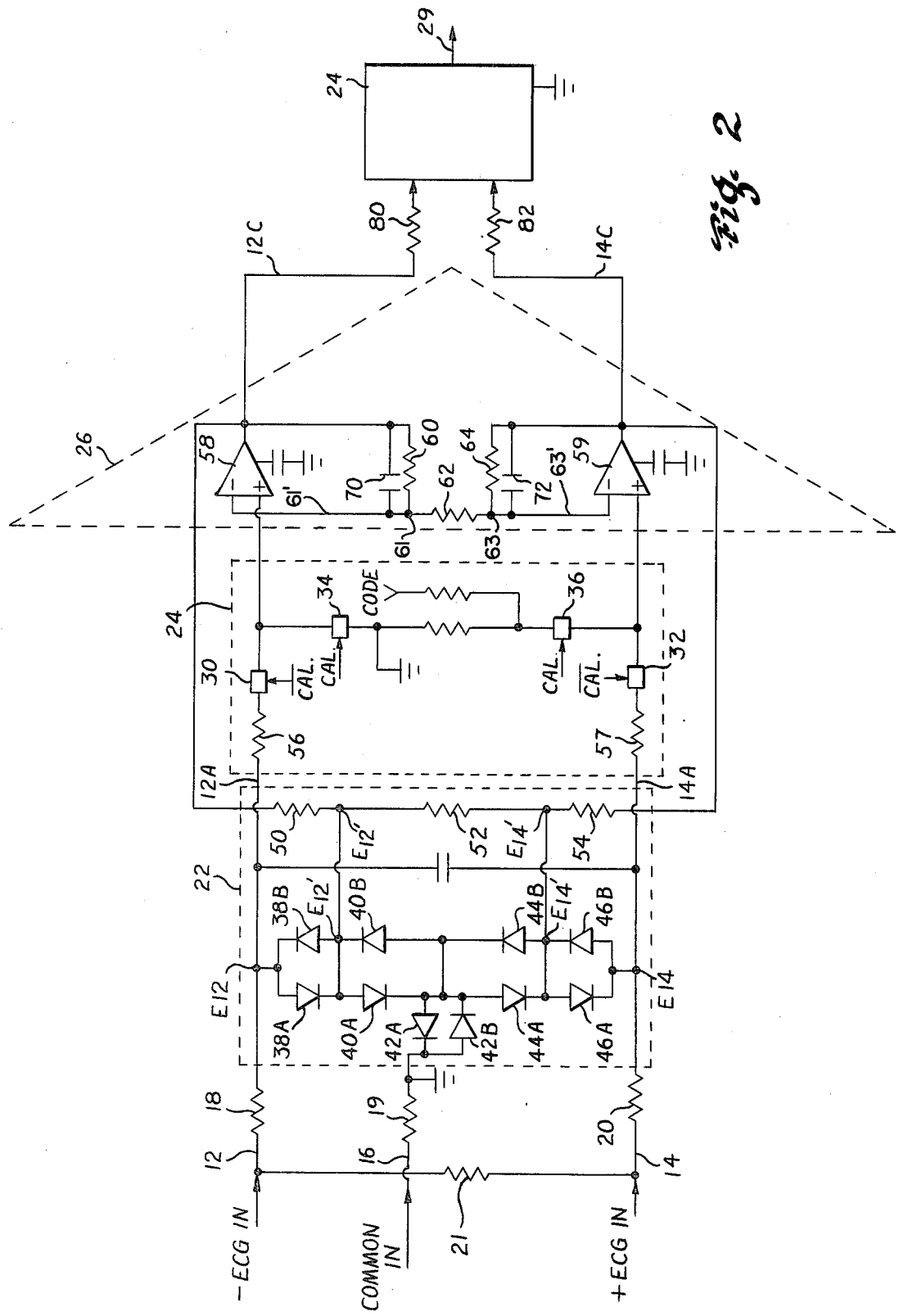
FIG. 2 is a more detailed schematic diagram of the circuitry of FIG. 1.

Referring to FIG. 2 for a detailed illustration of the preferred embodiment of the invention, it is seen that conductor 16 from the patient's right leg is connected, through resistor 19, to a common reference potential, in this instance a floating ground, but not necessarily earth ground. Typically, the differential voltage between electrodes RA and LA associated with conductors 12 and 14 is on the order of several hundred millivolts, with the AC differential voltage of interest being of the order of one millivolt. The common mode voltage may typically be several hundred millivolts. Series input resistors 18, 19 and 20 may typically be large, i.e., 100 K ohm, to limit fault currents. A large resistance 21, i.e., 3 M ohm, is connected across the patient leads 12 and 14 prior to input resistors 18 and 20 to serve as a passive drain for discharging any excessive electrical charge arising due to electrolytic cell imbalance in the patient 10.

From time to time, as during defibrillation or shortly after the placement or movement of electrodes on the patient or at certain other times, the potential of the signal appearing on conductor 12 and/or 14 relative to one another and/or to the reference electrode 16 may be sufficiently large to possibly damage the circuitry of differential amplifier 26 or, more likely, the CMOS switches 30, 32, 34 and/or 36 associated with switching unit 24. In the illustrated embodiment, input common mode and/or differential voltages below about 0.3 volts afford linear operation, while those above 2 volts are considered to be excessive and, accordingly, protection means thereagainst are provided. Distortion is permitted between the 0.3 and 2 volt levels. The protection circuitry 22 includes, in part, a clamping network utilizing diode action to effectively short circuit excessive input potentials. More specifically, the clamping network employs a ladder network of oppositely poled parallel connected diodes of a type selected to have low leakage, i.e., Type FD333. A first such ladder network of clamping diodes is comprised of the serial connection of oppositely poled parallel pairs of diodes 38A, 38B in series with 40A, 40B in turn in series with 42A, 42B. This series plurality of diode pairs is connected between conductor 12A and the ground reference potential. A second similar arrangement extends between conductor 14A and the ground reference potential and is comprised of oppositely poled parallel pair 46A, 46B is series with oppositely poled parallel pair 44A, 44B in turn in series with the previously described oppositely poled parallel pair 42A, 42B. It will be appreciated that diode pair 42A, 42B is common to both the path from 12A to ground and 14A to ground. The oppositely poled configuration of the diodes affords clamping protection for over-voltages of either polarity, as is well known. In the present instance, the number of diode-pairs in series between either conductor 12A or 14A and ground is there, two pairs of which determine the threshold above which the third pair conducts. When the amplifier 26 is not powered, these three diode-pairs establish the approximately 2 volt maximum at which the diodes are heavily conducting and clamping. It will be noted that for purely differential voltages appearing across conductors 12A, 14A when the common mode voltage is zero, the diode-pair 42 is not conducting and therefore, the differential threshold is determined by the two diode-pairs 40, 44 above which threshold, pairs 38 and 46 will conduct.

If the protection circuit 22 were considered complete with the ladder network of clamping diodes described above, it would generally operate to mutually electrically separate conductors 12A, 14A and the ground reference potential, such that the small signal voltages appearing on conductors 12A, 14A are subsequently applied to the inputs of differential amplifier 26. Furthermore, should these potentials become excessive, the appropriate series string of diodes would become forward biased into conduction and serve to clamp the respective input. However, it is important to note that such a diode clamping arrangement typically creates a leakage current path therethrough even though the diodes are reverse biased and substantially nonconducting. Even though the impedance of the leakage path through the diodes is relatively high, the nonlinear leakage current is sufficient in series with an input resistor such as 18 or 20 to distort the potential $E_{12}$ or $E_{14}$ appearing on conductors 12A or 14A respectively, thereby distorting the input to differential amplifier 26. In order to avoid the aforementioned leakage currents through the clamping means, the overload protection circuit 22 additionally includes driven guard circuitry which includes a voltage divider comprised of resistors 50, 52 and 54 which will be described hereinafter in greater detail.

The input signal potential appearing on conductor 12A at its junction with clamping diodes 38A, 38B is designated $E_{12}$ and similarly, the input signal potential on conductor 14A at its junction with clamping diodes 46A, 46B is designated $E_{14}$. Those potentials, attenuated only slightly by relatively small series resistors 56, 57 and conductors 12A, 14A respectively, are passed through normally closed CMOS calibration switches 30, 32 respectively to the inputs of differential amplifier 26. Differential amplifier 26 is comprised of a pair of operational amplifiers 58 and 59, the noninverting inputs of each serving as the respective pair of inputs to the differential amplifier 26. Differential amplifier 26 and accordingly operational amplifiers 58, 59 and the circuitry therewith are designed to present unity gain to any common mode voltage appearing at the input but to provide a gain factor of eight to the input signal differential. A symmetrical voltage divider network comprised of serial resistors 60, 62 and 64 is connected across the output conductors 12C, 14C of operational amplifiers 58, 59 respectively. To provide the 8X gain factor for amplifiers 58, 59, resistor 62 (57.6 K ohm) has a value which is one-eighth that of the total series resistance of the resistances 60, 62 and 64. Accordingly, resistors 60 and 64 each have a value of 200 K ohm.

At the junction or tap 61 between resistors 60 and 62 there is provided a feedback conductor 61' connected to the inverting input of operational amplifier 58. Similarly, at the junction or tap 63 between resistors 62 and 64 there is provided a feedback conductor 63' connected to the inverting input of operational amplifier 59. Through use of the feedback to the inverting inputs of amplifiers 58 and 59 respectively, the potentials appearing at those inputs and, accordingly, at junctions 61 and 63 respectively are substantially identical to the input potentials to the respective noninverting inputs of those amplifiers. Stated another way, because the input to operational amplifier 58 on conductor 12B is only slightly less than $E_{12}$, substantially that same potential designated $E_{12}$, will appear at junction 61. Similarly, because the potential on the noninverting input of amplifier 59 is only slightly less than $E_{14}$, the potential appearing at junction 63 is substantially the same value and designated $E_{14'}$.

Thus it will be seen that the potentials $E_{12}$, and $E_{14}$, appearing at the opposite terminals of resistor 62 are substantially the same as those potentials $E_{12}$ and $E_{14}$ appearing on conductors 12A and 14A respectively at the opposite ends of the diode clamping circuitry. Capacitors 70 and 72 are connected in parallel with resistors 60 and 64 respectively for reducing the differential bandwidth of amplifier 26.

The outputs of operational amplifiers 58 and 59 appear respectively on conductors 12C and 14C which in turn comprise the differential output from differential amplifier 26. The conductors 12C and 14C may serve, through resistors 80 and 82, as the differential input to amplifier 24 having the single-ended output 29. Resistors 80 and 82 may be respectively incorporated in two arms of a bridge network which includes the amplifier 24, which circuitry is described in greater detail in co-pending U.S. application Ser. No. 884,322 filed Mar. 7, 1978. by T. K. Naylor and E. Dokus for Improved Fast-Recovery Circuit.

The voltage divider comprised of resistors 50, 52 and 54 and comprising part of protection circuit 22 is connected across the output conductors 12C, 14C from amplifier 26, as is the voltage divider comprised of resistors 60, 62 and 64. Although not necessarily of the same resistive values as resistors 60, 62 and 64, the voltage divider comprised of resistors 50, 52 and 54 is proportioned or scaled identically with the former voltage divider. In the illustrated embodiment, the actual resistive values of resistors 50, 52 and 54 do correspond exactly with resistors 60, 62 and 64 respectively. However, the basic requirement is only that the value of resistor 52 be one-eighth of the total value of resistors 50, 52 and 54 and that the values of resistors 50 and 54 equal one another. In this way, it will be appreciated that the potential appearing at the junction or tap between resistors 50 and 52 is substantially the same as that appearing at junction 61, or in other words, $E_{12'}$. Similarly, the potential appearing at the junction or tap between resistors 52 and 54 corresponds with that appearing at junction 63, or in other words, $E_{14'}$. Thus, at low frequencies, substantially the same potential applied to conductor 12A is applied to the cathode of diode 38A and the anode of diode 38B and, similarly, substantially the same potential applied to conductor 14A is applied to the anode of diode 46A and the cathode of diode 46B. If high-frequency guarding is desired, resistors 50 and 54 should each be bypassed by capacitors. Because the potential difference or the $\Delta V$ across each of the diode pairs 38A, 38B and 46A, 46B respectively is substantially zero, then in accordance with Ohm's law there may be no leakage current flow through those diodes. In that way, the protection circuit 22 does not load the input to amplifier 26 during normal conditions of small signal linear operation. The voltage divider network of resistors 50, 52 and 54 for providing guard potentials $E_{12'}$ and $E_{14'}$ to the diode clamping circuit is separate from the voltage divider comprised of resistors 60, 62 and 64 to prevent the diodes from loading the latter network.

Should the voltage on conductors 12A, 14A become excessive, either the outputs of amplifiers 58 and 59 will reach their respective power supply limits and/or any two or more diode-pairs 40, 42, 44 will conduct enough to load the resistive divider 50, 52, 54 so that the guard voltages $E_{12'}$ and $E_{14'}$ applied to the clamping network will no longer follow the voltage on conductors 12A, 14A. Accordingly, the appropriate section or sections of the diode network, viz., pairs 38, 46, will begin to conduct and clamp the input to differential amplifier 26 such that further increase in the input current and potential thereto is substantially prevented. The large series resistors 18, 19 and 20 limit current through the diodes during clamping. It will be appreciated that the diode protection circuit of the present invention is structured to clamp the input to differential amplifier 26 for both excessive differential voltages and excessive common mode voltages applied to the input.

During any intervals of excess input voltage, the diode protection network will begin conducting and thereby load and clamp the input to not only differential amplifier 26 but also the relatively delicate circuitry of the CMOS calibration switches 30, 32, 34 and 36. Calibration switches 30 and 32 are normally closed to permit application of the ECG signal to the inputs of amplifier 26. However, during a calibration procedure, switches 30 and 32 are opened and switches 34 and 36 are closed to apply some predetermined calibration code signal to the inputs of amplifier 26. In the event the power supply to differential amplifier 26 and calibration switches 30, 32 is lost for any reason, it will be appreciated that the driven guard voltages $E_{12'}$ and $E_{14'}$ applied to the diode clamping network will similarly be lost. In such instance, the clamping diodes revert to the simple diode limiters of the prior art. Then, however, it is necessary to limit residual input currents to the current-intolerant CMOS switches 30, 32 by inclusion of the small series resistors 56, 57 in the respective input conductors before the switches.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

I claim:
1. An input overload protection circuit comprising:
   a high impedance differential amplifier having a pair of inputs;
   a pair of input conductors operatively connected to said respective pair of inputs of said differential amplifier for conducting signal thereto;
   a third conductor connected to a reference potential;
   a first serial plurality of diode-action clamping means connected intermediate one conductor of said pair and said third conductor;
   a second serial plurality of diode-action clamping means connected intermediate the other conductor of said pair and said third conductor; and
   guard means responsive to the respective signal voltage at that end of said respective first and second plurality of clamping means connected respectively to said one and said other conductors of said pair for applying substantially said respective signal voltage to said respective first and second plurality of clamping means intermediate the respective ends thereof, thereby to substantially prevent leakage current from flowing through said clamping means from said pair of conductors.

2. The protection circuit of claim 1 wherein at least one diode-action clamping means in both said first and second pluralities is common to both said first and second pluralities.

3. The protection circuit of claim 2 wherein said at least one clamping means common to both said first and second pluralities of clamping means includes that one connected most directly to said third conductor.

4. The protection circuit of claim 2 wherein said differential amplifier comprises a pair of operational amplifiers each having a different one of said pair of input conductors respectively connected to the noninverting input thereof, said input conductors applying substantially said respective signal voltages to said respective operational amplifier inputs, a first voltage divider network having its opposite ends connected to the respective outputs of said pair of operational amplifiers, and first and second spaced taps on said divider respectively connected to the inverting inputs of said pair of operational amplifiers for completing respective feedback paths thereto, the voltages appearing at said first and second taps being substantially the same as said signal voltages appearing on the respective conductors of said pair; and said guard means comprises a second voltage divider network having its opposite ends connected to the respective outputs of said pair of operational amplifiers and having respective first and second taps thereon with the same division ratio as said taps on said first voltage divider, said first and second taps of said second voltage divider being connected to apply said respective signal voltages to said respective first and second plurality of clamping means for preventing leakage current from flowing.

5. The protection circuit of claim 4 wherein both said first and second voltage divider networks are resistive, each having first, second and third resistances respectively divided by said first and second taps, said first and third resistances of each particular divider being of equal value.

6. The protection circuit of claim 3 including circuit element means intolerant of large currents and connected in series in at least one conductor of said pair intermediate said clamping means and the respective input to said amplifier, said current-intolerant means being adversely affected by currents above a small value, and series resistance means of low ohmic value in the respective said conductors between said clamping means and said current-intolerant element for limiting residual input current to the latter.

* * * * *

UNITED STATES PATENT AND TRADEMARK OFFICE
CERTIFICATE OF CORRECTION

PATENT NO. : 4,158,863

DATED : June 19, 1979

INVENTOR(S) : Thomas K. Naylor

It is certified that error appears in the above-identified patent and that said Letters Patent are hereby corrected as shown below:

In column 4, line 21, delete "40a" and insert --40A--;

In column 4, line 26, delete "is" and insert --in--; and

In column 4, line 36, delete "there" and insert --three--.

Signed and Sealed this

Twenty-seventh Day of November 1979

[SEAL]

Attest:

RUTH C. MASON
*Attesting Officer*

LUTRELLE F. PARKER
*Acting Commissioner of Patents and Trademarks*